Figure 1:
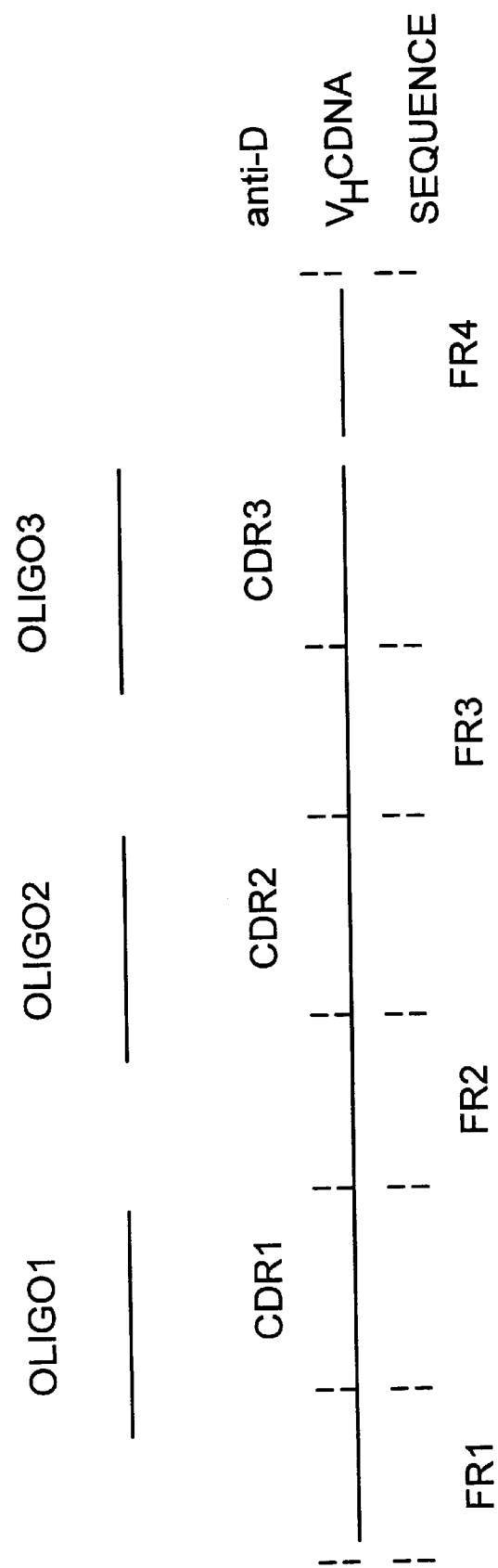
Figure 1:

United States Patent [19]

Hughes-Jones

[11] Patent Number: 5,919,910
[45] Date of Patent: Jul. 6, 1999

[54] MONOCLONAL ANTIBODIES

[75] Inventor: Nevin Campbell Hughes-Jones, Royston, United Kingdom

[73] Assignee: National Blood Authority, Hertfordshire, United Kingdom

[21] Appl. No.: 08/477,553

[22] Filed: Jun. 7, 1995

Related U.S. Application Data

[62] Division of application No. 07/856,034, filed as application No. PCT/EP90/01964, Nov. 13, 1990, Pat. No. 5,831,063.

[30] Foreign Application Priority Data

Nov. 13, 1989 [GB] United Kingdom ................. 8925590

[51] Int. Cl.$^6$ .......................... C07K 19/00; C07H 21/04; A61K 39/395
[52] U.S. Cl. ..................... 530/387.3; 536/23.53; 435/320.1; 435/343; 424/133.1; 424/153.1
[58] Field of Search .................... 530/387.3; 435/320.1, 435/343; 536/23.53; 424/133.1, 153.1

[56] References Cited

FOREIGN PATENT DOCUMENTS

A-0239400 9/1987 European Pat. Off. .
2189506 10/1987 United Kingdom .

OTHER PUBLICATIONS

Morrison et al., *Clin. Chem.*, 34(9):1668 (Sep. 1988).
Riechmann et al., *Nature*, 332:323–327 (Mar. 1988).
Verhoeyen et al., *Bio Essays*, 8(2):74–78 (Feb.–Mar. 1988).

*Primary Examiner*—Frank C. Eisenschenk
*Attorney, Agent, or Firm*—Burns, Doane, Swecker & Mathis, L.L.P.

[57] ABSTRACT

The present invention provides DNA sequences encoding complementarity determining regions of variable domains of human anti-RhD antibodies and their use in the production of recombinant chimeric antibody molecules. Chimeric antibody molecules against the Rhesus (D) antigen or an antigen binding fragment thereof, as well as anti-Rhesus (D) reagents and pharmaceutical compositions comprising said chimeric antibodies are also provided.

31 Claims, 13 Drawing Sheets

```
1   CAGTCTGTGTTGACGCAGCCGCCCTCAGTGTCTGCCCCCAGGACAGAAGGTCACCATC  60
    Q  S  V  L  T  Q  P  P  S  V  S  A  A  P  G  Q  K  V  T  I

61  TCCTGCTCTCCGGAACCAGCTCCAACATTGGGAATAATTATGTATCCTGGTATCAGCAGCTC  120
    S  C  S  G  T  S  S  N  I  G  N  N  Y  V  S  W  Y  Q  Q  L
                    <------CDR1------>

121 CCAGGAACAGCCCCCAAACTCCTCATTTATGACAATAATAAGCGACCCTCAGGGATTCCT  180
    P  G  T  A  P  K  L  L  I  Y  D  N  N  K  R  P  S  G  I  P
                                <------CDR2------>

181 GACCGATTCTCTGGCTCCAAGTCTGGCACGTCAGCCACCCTGGGCATCACCGGACTCCGG  240
    D  R  F  S  G  S  K  S  G  T  S  A  T  L  G  I  T  G  L  R

241 ACTGGGGACGAGGCCGATTATTACTGCGCAACATGGGATAGCAGCCTGAGTGCTGTGGTG  300
    T  G  D  E  A  D  Y  Y  C  A  T  W  D  S  S  L  S  A  V  V
                                    <------CDR3

301 TTCGGGGGAGGGACCAAGCTGACCGTCCTA AGT  333
    F  G  G  G  T  K  L  T  V  L  S
    ------>
```

FIG. 2

```
  1 TCCTATGTGCTGACTCAGCCACCCTCGGTGTCAGTGGCCCCAGGACAGACGGCCAGGATT  60
    S  Y  V  L  T  Q  P  P  S  V  S  V  A  P  G  Q  T  A  R  I

61 ACCTGTGGGGAAACAACATTGGACGTAAAAGTGTGCACTGGTACCAGCAGAAGCCAGGC 120
    T  C  G  G  N  N  I  G  R  K  S  V  H  W  Y  Q  Q  K  P  G
    <———————— CDR1 ————————>

121 CAGGCCCCTGTGCTCGTTGTGTCTATGGTGCTAGCGACCGGCCCTCAGGGATCCCTGAGCGA 180
    Q  A  P  V  L  V  V  Y  G  A  S  D  R  P  S  G  I  P  E  R
                                <——————— CDR2 ———————>

181 TTCTCTGGCTCCAACTCTGGGAACACGGCCACCCTGACCATCAGCAGGGTCGCAGCCGGG 240
    F  S  G  S  N  S  G  N  T  A  T  L  T  I  S  R  V  A  A  G

241 GATGAGGCCGACTATTACTGTCAGGTGTGGGATAGTAGTGCTCATCCGGGGGTGGTA 300
    D  E  A  D  Y  Y  C  Q  V  W  D  S  S  A  H  P  G  V  V ———>
                         <———————————— CDR3

301 TTCGGCGGAGGGACCAAGCTGACCGTCCTAGGT 333
    F  G  G  G  T  K  L  T  V  L  G
    ————————>
```

FIG. 3

```
  1  CAGCTGCGGCTGCAGGAGTCGGGCCCAGGACTGGTGAAGCCTTCGGAGACCCTGTCCCTC  60
     Q  L  R  L  Q  E  S  G  P  G  L  V  K  P  S  E  T  L  S  L

61  ACCTGCAGTGTCTCTGGTGGCTCCGTCAGCAGTGGTGGTCTCTACTGGGGCTGGGTCCGC  120
     T  C  S  V  S  G  G  S  V  S  S  G  G  L  Y  W  G  W  V  R
                                       <------- CDR1 ------->

121  CAGCCCCCAGGGAAGGGGCTCGAATGGATTGGCAGTATATTTATAGTGGGAGCACCTAC  180
     Q  P  P  G  K  G  L  E  W  I  G  S  I  F  Y  S  G  S  T  Y
                                       <--------- CDR2

181  TACAATCCCTCCCTCAAGAGCCGAGTCACCATATCCGTAGACACGTTGAAGAATAACTTC  240
     Y  N  P  S  L  K  S  R  V  T  I  S  V  D  T  L  K  N  N  F
     ------->

241  TCCCTGAAGCTGAGTTCTGTGACCGCAGCAGACACGGCTGTTTATTACTGTACGAGACCA  300
     S  L  K  L  S  S  V  T  A  A  D  T  A  V  Y  Y  C  T  R  P
                                                            <---

301  GGCTATGGCGACACCTCGGTACGGAAGAGGGTTTGGAATATGGACCTCTGGGGCCAAGGG  360
     G  Y  G  D  T  S  V  R  K  R  V  W  N  M  D  L  W  G  Q  G
     ------------------- CDR3 ------------------->

361  ACCACGGTCACCGTCTCCTCG  381
     T  T  V  T  V  S  S
```

FIG. 4

```
  1 CAGGTGCAGCTGCAGGAGTCGGGCCCAGGACTGGTGAAGCCTTCGGAGACCCTGTCCGTC   60
    Q  V  Q  L  Q  E  S  G  P  G  L  V  K  P  S  E  T  L  S  V

61 ACCTGCACTGTCTCTGGTGGCTCCGTCAGTAGTTCCTACTGGAGCTGGATCCGGCAGCCC  120
    T  C  T  V  S  G  G  S  V  S  S  S  Y  W  S  W  I  R  Q  P
                                   <------ CDR1 ------>

121 CCAGGGAAGGGACCGGAGTGGATTGGGTATATCTATTACAGTGGGAGCACCAACTACAAC  180
    P  G  K  G  P  E  W  I  G  Y  I  Y  Y  S  G  S  T  N  Y  N
                                   <------------ CDR2

181 CCCTCCCTCAGGAGTCGAGTCACCATATCAGTAGACACGTCCAAGAACCAGTTCTCCCTG  240
    P  S  L  R  S  R  V  T  I  S  V  D  T  S  K  N  Q  F  S  L
    ------>

241 AAGCTGGGCTCTGTGACCGCTGCGGACACGGCCGTGTATTACTGTGCGAGAGTTTTGGTT  300
    K  L  G  S  V  T  A  A  D  T  A  V  Y  Y  C  A  R  V  L  V
                                                        <------

301 TCCCGTACGATTTCACAGTACTCCTATTACATGGACGTCTGGGGCAAAGGGACCACGGTC  360
    S  R  T  I  S  Q  Y  S  Y  Y  M  D  V  W  G  K  G  T  T  V
    ------------ CDR3 ------------>

361 ACCGTGTCCTCA   372
    T  V  S  S

FIG. 5
```

```
1    ------PCR PRIMER------     CGCAGGACTGTTGAAGCCTTCGGAGACCCTGTCCCTC  60
                                 A  G  L  L  K  P  S  E  T  L  S  L

61   ACCTGCGCTGTCTATGGTGGGTCCTTCAGTGGTTACTACTGGAGCTGGATCCGCCAGCCT  120
      T  C  A  V  Y  G  G  S  F  S  G  Y  Y  W  S  W  I  R  Q  P
                                     <------ CDR1 ------>

121  CCAGGGAAGGGGCTGGAGTGGATTGGGGAAATCAATCATAGTGGAAGGACCAACTACAAC  180
      P  G  K  G  L  E  W  I  G  E  I  N  H  S  G  R  T  N  Y  N
                                    <------ CDR2

181  CCGTCCCTCAAGACTCGAGTCACCATATCAGTAGACACGTCCAAGAACCAGTTCTCCCTG  240
      P  S  L  K  T  R  V  T  I  S  V  D  T  S  K  N  Q  F  S  L
                                -------->

241  AAGCTGAGTTCTGTGACCGCCGCGGACACGGCTGTGTATTACTGTGCGAGACTGTGGCTC  300
      K  L  S  S  V  T  A  A  D  T  A  V  Y  Y  C  A  R  L  W  L
                                                           <------

301  GATGGACACATGGGTACAAGTTTGACTACTGGGGCCAGGGAACCCT  ------PCR PRIMER------  360
      D  G  H  M  G  Y  K  F  D  Y  W  G  Q  G  T  L
     ------ CDR3 ------>
```

FIG. 6

```
  1 CAGGTGCATCTACAGCAGTGGGGCACAGGGCTGTTGAAGCCTTCGGAGACCCTGTCCCTC  60
    Q  V  H  L  Q  Q  W  G  T  G  L  L  K  P  S  E  T  L  S  L

61 ACCTGCGCTGTCCATGGTGGGTCCTTCAATGTTTACTACTGGACCTGGATCCGCCAGCCC 120
    T  C  A  V  H  G  G  S  F  N  V  Y  Y  W  T  W  I  R  Q  P
                        <------- CDR1 ------->

121 CCAGGAAAGGCGCTGGAGTGGATTGGGGAAATCAATCATAGTGGAGGCGCCAACTACAAT 180
    P  G  K  A  L  E  W  I  G  E  I  N  H  S  G  G  A  N  Y  N
                                <-------- CDR2

181 CCGTCCCTCAAGAGTCGAGTCACCATGTCAGCAGACACGTCCAAGAACCAGTTCTCCCTG 240
    P  S  L  K  S  R  V  T  M  S  A  D  T  S  K  N  Q  F  S  L
    --------->

241 AAACTGACCTCTGTGACCGCGGCCGACACGGCTGTGTTTATTGTGCGAGAGGCCGGTCC  300
    K  L  T  S  V  T  A  A  D  T  A  V  F  Y  C  A  R  G  R  S
                                                        <-----

301 CGTTATAGTGGTTACGGCTTCTACTCCGGCATGGACGTCTGGGGCCCAGGGACCACGGTC 360
    R  Y  S  G  Y  G  F  Y  S  G  M  D  V  W  G  P  G  T  T  V
    ------- CDR3 ------->

361 ACCGTCTCCTCA 372
    T  V  S  S
```

FIG. 7

1   CAGGTGCAGCTACAGCAGTGGGGCGCAGGACTGTTGAAGCCTTCGGAGACCCTGTCCCTC   60
    Q  V  Q  L  Q  Q  W  G  A  G  L  L  K  P  S  E  T  L  S  L

61  ACCTGCGCTGTCTATGGTGGGTCCTTCAGTGGTTACTACTGGAACTGGATCCGCCAGCCC  120
    T  C  A  V  Y  G  G  S  F  S  G  Y  Y  W  N  W  I  R  Q  P
                          <------- CDR1 ------->

121 CCAGGGAAGGGGCTGGAGTGGATTGGGGAAATCATTCATAGTGGAAGCACCAACTACAAC  180
    P  G  K  G  L  E  W  I  G  E  I  I  H  S  G  S  T  N  Y  N
                                  <------------ CDR2

181 CCGTCCCTCAAGAGTCGAGTCACCATGTCAGTAGACACGTCCAAGAACCAGTTCTCCCTG  240
    P  S  L  K  S  R  V  T  M  S  V  D  T  S  K  N  Q  F  S  L
    ------------>

241 AAGCTGAGCTCTGTGACCGCCGCGGACACGGCTGTGTATTACTGTGCGAGAGGCTTAGAA  300
    K  L  S  S  V  T  A  A  D  T  A  V  Y  Y  C  A  R  G  L  E
                                                          <----

301 CGTCCGATTAGGAACCAGCTGCTAAACCGTCTCGGTTACTACTACATGGACGTCTGGGGCAAA  360
    R  P  I  R  N  Q  L  L  N  R  L  G  Y  Y  Y  M  D  V  W  G  K
    -------------------- CDR3 ------------------------->

361 GGGACCACGGTCACCGTCTCCTCA   384
    G  T  T  V  T  V  S  S

FIG. 8

```
1   CAGGTGCAGCTACAGCAGTGGGGCGCAGGACTGTTGAAGCCTTCGGAGACCCTGTCCCTC   60
    Q  V  Q  L  Q  Q  W  G  A  G  L  L  K  P  S  E  T  L  S  L

61  ACCTGCGCTGTCTATGGTGGGTCCTTCAGTGGTTACTACTGGAGCTGGATCCGCCAGCCC  120
    T  C  A  V  Y  G  G  S  F  S  G  Y  Y  W  S  W  I  R  Q  P
                              <------- CDR1 ------->

121 CCAGGGAAGGGCTGGAGTGGATTGGGGAAATCAGTCGTCGTGGAAGCACCAACTACAAC  180
    P  G  K  G  L  E  W  I  G  E  I  S  R  R  G  S  T  N  Y  N
                                  ------- CDR2

181 CCGTCCCTCAAGAGTCGAGTCGCCATATCAGTAGACACGTCCAAGAACCAGTTCTCCCTG  240
    P  S  L  K  S  R  V  A  I  S  V  D  T  S  K  N  Q  F  S  L
          ------->

241 AAGGTGAGGTCTGTGACCGCCGCGGACACGGCTGTGTATTACTGTGCGAGAGCCTTGGAC  300
    K  V  R  S  V  T  A  A  D  T  A  V  Y  Y  C  A  R  A  L  D
                                                            <---

301 TACATCTCCTTGGATTACGGTATGGACGTCTGGGGCCAAGGGACCACGGTCACCGTCTCC  360
    Y  I  S  L  D  Y  G  M  D  V  W  G  Q  G  T  T  V  T  V  S
    ------- CDR3 ------->

361 TCA  363
    S
```

FIG. 9

```
  1   ----------PCR PRIMER----------  GGGAGGCGTGGTCCAGCCTGGGAGGTTCCTGAGACTC    60
                                       G  G  V  V  Q  P  G  R  F  L  R  L

61   TCCTGTGCAGCGTCTGGATTCACCTTCAGTAGCTATGGCATGCACTGGGTCCGCCAGGCT           120
       S  C  A  A  S  G  F  T  F  S  S  Y  G  M  H  W  V  R  Q  A
                                     <------ CDR1 ------>

121   CCAGGCAAGGGGCTGGAGTGGGTGGCACTTATATGGTATGATGGAAGTAATAAAGAATAT          180
       P  G  K  G  L  E  W  V  A  L  I  W  Y  D  G  S  N  K  E  Y
                                  <------------ CDR2

181   GCAGACTTCGTGAAGGGCCGATTCACCATCTCCAGAGACAATTCCAAGAATACACTGTAT         240
       A  D  F  V  K  G  R  F  T  I  S  R  D  N  S  K  N  T  L  Y
       ------>

241   CTGCAAATGAACAGCCTGAGAGCCGAGGACACGGCTGTGTATTACTGTGCGACAGATAGT        300
       L  Q  M  N  S  L  R  A  E  D  T  A  V  Y  Y  C  A  T  D  S
                                                                <----

301   CCCAAAATGAGGGCTGGAAGTATGTTTCGGTTTTTTACATGGACGTCTGGGGCAAAGGG         360
       P  K  M  R  A  G  S  M  F  R  Y  Y  Y  Y  M  D  V  W  G  K  G
       ----------------- CDR3 ----------------->

361   ACCAC ------PCR PRIMER------    381
       T
```

FIG. 10

```
1    ------PCR PRIMER------ GGGAGGCTTAGTTCAGCCTGGGGGTCCCTGAGACTC    60
                                G  G  L  V  Q  P  G  G  S  L  R  L

61   TCCTGTGCAGCCTCTGGATTCACCTTCAGTAGTTACTGGATGCACTGGGTCCGCCAAGCT   120
      S  C  A  A  S  G  F  T  F  S  S  Y  W  M  H  W  V  R  Q  A
                                    <------CDR1------>

121  CCAGGGAAGGGGCTGGTGTGGGTCTCACGTATTAATAGTTATGGAATTAGCACAAGTTAC   180
      P  G  K  G  L  V  W  V  S  R  I  N  S  Y  G  I  S  T  S  Y
                                   <------              CDR2

181  GCGAACTCCGTGAAGGGCCGATTCACCATCTCCAGAGACAACGCCAAGAACACGCTGTAT   240
      A  N  S  V  K  G  R  F  T  I  S  R  D  N  A  K  N  T  L  Y
                       ------>

241  CTGCAAATGAACACTCTGAGAGGGGAGGACACGGGTCTGTATTACTGTGCAAGAGGAGAG   300
      L  Q  M  N  T  L  R  A  E  D  T  A  V  Y  Y  C  A  R  G  E
                                                              <------

301  CGCATAGCAGCTCGTCTCTTGTCGGGGGCGTCTGGGGCCAAGGGACC   360
      R  I  A  A  R  L  L  S  G  G  Y  G  M  D  V  W  G  Q  G  T
                    CDR3                           ------>

361  AC      ------PCR PRIMER------   378
```

FIG. 11

```
1    -----PCR PRIMER-----         GGGAGGCGTGGTCCAGCCTGGGAGGTCCCTGAGACTC    60
                                  G  G  V  V  Q  P  G  R  S  L  R  L

61   TCCTGTGCAGCGTCTGGATTCACCTTTAGTAGCTATGGCATGCACTGGGTCCGCCAGGCT    120
     S  C  A  A  S  G  F  T  F  S  S  Y  G  M  H  W  V  R  Q  A
                                         <----- CDR1 ----->

121  CCAGGCAAGGGGCTGGAGTGGGTGGCAGTGATATGGTATGATGGAAGTAATAAGTACTAT    180
     P  G  K  G  L  E  W  V  A  V  I  W  Y  D  G  S  N  K  Y  Y
                                   <-------------- CDR2

181  GCAGAGTCCGTGAAGGGGCGATTCACCATCTCCAGAGACAATTCCAAGAACACGCTGTAT    240
     A  E  S  V  K  G  R  F  T  I  S  R  D  N  S  K  N  T  L  Y
     ----------->

241  CTGCAAATGAACAGCCTGAGAGCCGAGGACACGGCTGTATATTACTGTGCGAGAGTCGTT    300
     L  Q  M  N  S  L  R  A  E  D  T  A  V  Y  Y  C  A  R  V  V
                                                          <-----

301  AGCAGCAACCGGTACTCTCTAAGTACTACTATTATTACTACTACTACATGGACGTCTGGGGGCAAAGGG    360
     S  S  N  R  Y  S  L  S  Y  Y  Y  Y  Y  Y  Y  M  D  V  W  G  K  G
     -------------- CDR3 -------------->

361  ACCAC  -----PCR PRIMER-----  381
     T
```

FIG. 12

```
  1   -----PCR PRIMER-----        GGGAGGCGTGGTCCAGCCTGGGAGGTCCCTGAGACTC    60
                                   G  G  V  V  Q  P  G  R  S  L  R  L

61   TCCTGTGCAGCGTCTGGATTCACCTTCAATAATTATGGCATGCACTGGGTCCGCCAGGCT         120
       S  C  A  A  S  G  F  T  F  N  N  Y  G  M  H  W  V  R  Q  A
                                    <-----CDR1----->

121   CCAGGCAAGGGGCTGGAGTGGGTGGCAGTTATATGGTATGATGGAAGTAATAAAAACTAT         180
       P  G  K  G  L  E  W  V  A  V  I  W  Y  D  G  S  N  K  N  Y
                                              -------- CDR2

181   GCAGACTCCGTGAAGGGCCGATTCACCATCTCCAGAGACAATTCCAAGAACACGCTGTAT         240
       A  D  S  V  K  G  R  F  T  I  S  R  D  N  S  K  N  T  L  Y
                      ----->

241   CTGCAAATGAACAGCCTGAGAGCCGAGGACACGGCTGTGTATTACTGTGCGAGAGAACGT         300
       L  Q  M  N  S  L  R  A  E  D  T  A  V  Y  Y  C  A  R  E  R
                                                              <-----

301   ACTACGATGTCTGGAGTGATCATTCCTCGCCGGTATTTGACTACTGGGGCCAGGGAACC         360
       T  T  M  S  G  V  I  I  P  R  R  Y  F  D  Y  W  G  Q  G  T
            -----------CDR3---------->

361   CG   -----PCR PRIMER-----   378
```

FIG. 13

MONOCLONAL ANTIBODIES

This application is a divisional of application Ser. No. 07/856,034, filed Jun. 23, 1992, now U.S. Pat. No. 5,831, 063, which is the national phase of PCT/EP90/01964 filed Nov. 13, 1990.

This invention relates to novel monoclonal anti-RhD antibodies prepared by recombinant DNA methods.

The Rhesus blood group system is a major antigenic constituent of the human red blood cell membrane; of this group, the RhD antigen is of particular clinical importance in relation to isoimmune reactions. An Rh D-individual with anti-RhD who receives RhD+ blood is liable to suffer substantial red blood cell (RBC) destruction due to the RhD phenotype incompatibility, and thus blood of donors must routinely be classified as RhD+ or RhD−. Anti RhD monoclonal antibodies (anti-D Mabs) are capable of providing blood-typing reagents of high specificity and reliability.

The RhD antigen is also responsible for haemolytic disease of the newborn (HDN). This condition arises in newborn RhD+ infants of RhD− mothers previously sensitised to RhD antigen as a result of IgG anti-RhD antibodies crossing the placeenta during pregnancy and causing foetal red blood cell (RBC) destruction. Sensitization of the RhD− mother to RhD antigen often occurs during the birth of an earlier RhD+ child due to some foetal RBCs catering the maternal circulation and being recognised as foreign by the maternal immune system. To reduce the incidence of HDN, it is routine practice in the United Kingdom and many other countries to give anti-RhD antibodies to RhD− mothers immediately after the birth of an RhD+ infant so that any RhD+ RBCs which may have entered the maternal circulation are rapidly removed.

The search for the most effective anti D Mabs has proved to be extremely time consuming, involving the isolation of B-lymphocytes from humans immunised against RhD, usually Rh−ve mothers who have given birth to Rh+ve children. Such lymphocytes are subjected to EBV treatment to provide an immortalised cell-line directly or the EBV-treated cells are hybridised with suitable mouse myeloma cells to provide a hydridoma: The cell-line or hybridoma may then be used to produce the anti-D Mab in the conventional way.

However, there are significant differences between anti-D Mabs in terms of their binding affinities for red cells, their ability to recognise D-variants such as $D^O$ and $D^{VI}$, and their ability to destroy target cells by phagocynosis or cell-mediated lysis. It is desirable, therefore, to have available a method of combining the favourable parameters of different anti-D Mabs or, indeed of combining the most favourable features of selected anti-D Mabs with Mabs of quite different specificities which present particular advantages, in order to produce so-called chimaeric Mabs.

The concept of building chimaeric Mabs, has been described by Jones et al (Nature 321, 522–525 (1986)) and Riechmann et al (Nature 332, 323–327 (1988)). Three dimensional studies have shown that immunoglobulins comprise essentially constant regions common to most Mabs and terminally situated variable domains associated with antigen binding.

It has been shown that the variable domains consist of two β-sheets joined by a disulphide bridge with their hydrophobic faces in contact. Sequence comparisons among heavy- and light-chain variable domains ($V_H$ and $V_L$ respectively) have revealed that each of these domains comprises three hypervariable domains or complementarity determining regions (CDRS) set in a framework of four relatively conserved regions, the framework regions (FRs).

The CDRs are primarily responsible for the recognition of specific antigens. The structure of the β-sheet framework is similar in different antibodies, as the packing together of $V_L$ and $V_H$ FRs is conserved and therefore the orientation of $V_L$ with respect to $V_H$ is fixed.

Genes coding for a number of Mabs are now available and the sequences coding for the variable regions $V_L$ and $V_H$ have been determined. It is thus possible to replace the latter sequences by DNA coding for $V_L$ and $V_H$ from different Mabs and indeed to construct the latter by incorporating DNA coding for chosen CDRs into DNA coding for a standard set of FRs. It is thus possible to construct genes coding for chimeric anti-D Mabs having the CDRs from anti-D Mabs possessing particularly desirable specificities or other properties and framework and constant regions derived from Mabs having other desirable properties.

It is a prerequisite of such construction that the amino acid sequences of the CDR regions of the chosen anti-D Mabs and/or the genes coding for them, should be known. The specific CDR gene sequences can then be syntliesised, conveniently by chemical synthesis of the appropriate oligonucleotides, and incorporated into DNA sequences coding for a standard set of FRs and the human (or other) constant region. Of course, the FRs may be identical with those of the Mab providing the constant region or, more conveniently, they may be a standard set of FRs which can be used generally in the synthesis of chimeric Mabs.

We have produced a number of anti-D Mabs of particular interest and have determined their amino acid sequences, thus making it possible for DNA sequences corresponding to their CDRs to be synthesised and incorporated into $V_H$ and $V_L$ sequences as described above. These may then be combined with DNA coding for the constant region to enable novel anti-D Mabs to be synthesised which may have lower, the same or higher binding ability.

Thus, according to one aspect we provide DNA sequences comprising oligonucleotides encoding CDR1, CDR2, and CDR3 regions of $V_H$ and $V_L$ domains of antibodies against the human RhD antigen, and functional equivalents thereof. In particular, we have investigated and sequenced eleven Mabs, namely a) FOG-B, b) PAG-1, c) MAD-2, d) FOG-1, e) FOM-1, f) FOM-A, g) BRAD-3, h) JAC-10, i) GAD-2, J) REG-A, K) HAM-B, whose heavy and light chain sequences are represented in FIGS. 2–14, of the accompanying drawings, and which have both varied and particularly useful binding specificities. The FIGS. 2 and 3 show the nucleotide and amino acid sequences of the light chain variable domains of the Mabs FOG-B and PAG-1. Corresponding sequences for the heavy chain variable domains of these two Mabs are shown in FIGS. 4 and 5, and sequences of the heavy chain variable domains of the Mabs MAD-2, FOG-1, FOM-A, BRAD-3, JAC-10, GAD-2, REG-A and HAM-B are shown in FIGS. 6–14 (SEQ ID NOS: 47–55).

Synthetic genes, for both heavy and light chains may be created by combining selected CDR 1, 2, and 3 regions, which may be selected from different antibody molecules having varied binding specificities.

Thus according to a further aspect, we provide DNA molecules coding for the heavy or light chain fragments of a monoclonal antibody or fragment thereof comprising CDR1, CDR2 and CDR3 encoding oligonucleotides from antibodies FOG-B, PAG-1, MAD-2, FOG-1, FOM-1, FOM-A, BRAD-3, JAC-10, GAD-2, REG-A and HAM-B as illustrated in FIGS. 2–14 (SEQ ID NOS: 43–55).

In order to create functional genes, such oligonucleotides must be incorporated into a backbone sequence such that when expressed, functional proteins result.

Thus according to a further aspect, we provide DNA molecules comprising a gene coding for the framework regions of a human antibody light or heavy chain having inserted therein in the correct CDR region, oligonucleotides encoding CDR1, CDR2 and CDR3 regions according to the present invention.

In the synthesis of a chimeric Mab in accordance with the invention, single stranded DNA coding for the $V_H$ region of a chosen Mab (not necessarily an anti-D Mab) is incorporated in single stranded form into a vector capable of producing single stranded DNA, such as the M13 bacteriophage. FIG. 1 shows diagrammatically the structure of a single stranded $V_H$ DNA including framework regions FR1 to FR4 with complementarity determining regions CDR1 to CDR3 of a Mab. These steps can be accomplished by conventional techniques such as those described in Riechmann et al (Nature, 332, 323–327, (1988)).

Three oligonucleotides may then be prepared corresponding to the CDR regions of the chosen anti-D Mab variable domain, eg the $V_H$ region of FOG-B as shown in FIG. 4, and will include several nucleotides on either side of each CDR region to permit hybridisation with the framework regions FR1 to FR4 (see FIG. 1). The sequences of the latter will normally be substantially homologous with those of the anti-D Mab (e.g. FOG-B) but since the oligonucleotides will normally be synthesised chemically, hybridisation may be ensured by matching the overlapping nucleotides exactly to the FRs 1 to 4. It may also be beneficial to modify the oligonucleotides to express the CDRs more efficiently in the eventual host cells.

The three oligonucleotides, shown in FIG. 1 as oligo 1 to oligo 3, may then be annealed to a single stranded $V_H$ DNA in the M13 vector and used as primers to synthesise second strand DNA containing the anti-D $V_H$ CDR sequences. This may be achieved conventionally using a suitable polymerase. Since the antibody specificity is determined solely by the three CDR regions, the actual $V_H$ gene chosen for the framework template is immaterial. All that is required is that there is sufficient homology of the three chosen oligonucleotides with the template. This is ensured by appropriate design of the terminal nucleotides of the synthetic oligonucleotide primers. Thus the second strand may contain sequences from substantially any human antibody heavy chain gene, so long as the resulting expressed protein posesses the desired binding parameters.

The double stranded M13 vector may then be used to transform a suitable host microorganism e.g. a conventional E. coli and one or more clones selected which contain the required anti-D $V_H$ specificity. The correct clone may be identified by DNA seqencing.

The corresponding $V_L$ DNA (e.g. for FOG-B) may be prepared in the same way.

The DNA coding for the $V_H$ and $V_L$ regions may then be excised from the above vectors and introduced into other vectors.

According to a further aspect, we provide DNA molecules being synthetic genes for chimaeric antibody, heavy or light chains when incorporated into vectors capable of expressing such antibody chains. Preferred vectors include mammalian expression vectors, such as pSV2gpt (heavy chains) and pSV2neo (light chains) containing DNA coding for the human constant region. Such vectors are readily available from a number of laboratories, or can readily be prepared by incorporating DNA coding for human constant region into known mammalian vectors.

The expression vectors so constructed may then be co-transfected into an appropriate cell-line e.g. a non-secreting IgG myeloma, for large scale production.

Thus according to a yet further aspect, the present invention provides each of the CDR polypeptides of the Mabs FOG-B, PAG-1, MAD-2, FOG-1, FOM-1, FOM-A, BRAD-3, JAC-I0, GAD-2, REG-A and HAM-B shown in FIGS. 2–14 of the accompanying drawings in single stranded or double stranded form in the absence of the constant and or framework regions of said Mabs.

According to a yet further aspect, the invention provides chimaeric antibody heavy and light chains of the variable domains comprising CDR polypeptide sequences of the present invention.

Knowledge of the antibody sequences according to the invention enables new chimaeric anti-D antibody molecules to be prepared, having appropriately designed binding specificities. These antibodies may be used for both therapy and diagnosis using presently known techniques.

According to a yet further aspect, we provide anti-RhD reagents comprising at least one antibody molecule according to the invention.

According to a still yet further aspect, we provide pharmaceutical compositions for use in passive immunisation to prevent haemolytic disease of the newborn comprising an antibody of the present invention together with at least one phamacologically acceptable carrier or diluent.

A sterile solution of such an antibody for human injection may be formulated in any physiologically acceptable aqueous medium, for example isotonic phosphate buffered saline or serum. Alternatively, the antibody may be supplied in a freeze-dried formulation ready for reconstitution prior to use.

EXAMPLE (1) Construction of Chimaeric Antibody Genes

Three oligonucleotide primers are synthesised using an Applied Biosystems machine according to the manufacturer's instructions and purified on an 8 M Urea/polyacrylamide gel (Sanger & Coulson, Febs Lett., 87, 107–110, 1978). The primers are designed to comprise in their central regions sequences complementary to the CDR1, CDR2 and CDR3 regions of the anti-RhD antibody PAG-1 heavy chain gene, as identified according to the criteria described by Kabat et al. (Sequences of Proteins of Immunological Interest, U.S. Department of Health and Social Services, 1987).

The central sequences are flanked at both their 5' and 3' termini by sequences of 10 nucleotides which hybridise to the termini of the corresponding framework region sequences adjacent to the CDR sequence of the heavy chain antibody gene NEWM (Poljack et al., Biochemistry 16, 3412–3420, 1977). The primers are then hybridised to the derived NEWM single stranded DNA heavy chain sequence in the M13 bacteriophage and the complementary strand of the heavy chain variable region extended using DNA polymerase (Neuberger et al., Nature 314, 268–270 (1985), Jones et al., Nature 321, 522–5 (1986)). The M13 vector also contains an appropriate arrangement for ultimate expression, i.e. a leader sequence, and unique HindIII and BamHI restriction sites.

A similar construct is prepared from oligonucleotide primers homologous to the CDR regions of the PAG-1 anti-RhD antibody light chain genes, and utilising the M13 vector in which $V_L$ and $J_L$ regions of the antibody gene PAV1 (Sun et al., Nucleic Acids Research 13, 4921–4934, 1985) are cloned.

(2) Expression of Antibody Polypeptides

The cloned genes for the $V_H$ domains are excised using HindIII and BamHI and cloned into pSV2gpt (Mulligan and Berg, PNAS 78, 2072–6, 1981). The cloned light chain genes are similarly excised and cloned into pSV2neo (Southern and Berg, J. Molec. Appl. Genetics 1 327–381, 1981). Sequences encloding IgGl constant regions are then inserted into the vectors (Riechmann et al., Nature 312, 323–7, (1988). Both vectors are then transfected by electroporation (Potter et al., PNAS 81, 7161–3, 1984) into the rat myeloma cell line YO (YB2/3.0 AG, 20) (Galfre and Milstein, Methods in Enzymology 73, 1–46, 1981) for antibody production.

---

I claim:

1. A chimeric antibody $V_H$ chain against a Rhesus D antigen or an antigen binding fragment thereof comprising a CDR1, CDR2 and a CDR3 region, said $V_H$ chain selected from the group consisting of:

(i) a $V_H$ chain comprising a CDR1 region encoded by the DNA sequence of AGTGGTGGTCTCTACTGGGGC [SEQ ID NO:1]; a CDR2 region encoded by the DNA sequence of AGTATATTTTATAGTGGGAGCAC-CTACTACAATCCCTC CCTCAAGAGC [SEQ ID NO: 12]; and a CDR3 region encoded by the DNA sequence of CCAGGCTATGGCGACACCTCGG-TACGGAAGAGGGTTTGGAATATGGACCTC [SEQ ID NO:23];

(ii) a $V_H$ chain comprising a CDR1 region encoded by the DNA sequence of AGTTCCTACTGGAGC [SEQ ID NO:2]; a CDR2 region encoded by the DNA sequence of TATATCTATTACAGTGGGAGCACCAAC-TACAACCCCTCCCTC AGGAGT [SEQ ID NO:13]; and a CDR3 region encoded by the DNA sequence of GTTTTGGTTTCCCGTACGATTTCACAG-TACTCCTATTACATGGACGTC [SEQ ID NO:25];

(iii) a $V_H$ chain comprising a CDR1 region encoded by the DNA sequence of GTTTACTACTGGACC [SEQ ID NO:4]; a CDR2 region encoded by the DNA sequence of GAAATCAATCATAGTGGAGGCGCCAAC-TACAATCCGTCC CTCAAGAGT [SEQ ID NO: 15]; and a CDR3 region encoded by the DNA sequence of GGCCGGTCCCGTTATAGTGGTTACGGCT-TCTACTCCGGCATGGACGTC [SEQ ID NO:27];

(iv) a V$_H$ chain comprising a CDR1 region encoded by the DNA sequence of GGTTACTACTGGAGC [SEQ ID NO:6]; a CDR2 region encoded by the DNA sequence of GAAATCAGTCGTCGTGGAAGCACCAAC-TACAACCCGTCCCTC AAGAGT [SEQ ID NO: 17]; and a CDR3 region encoded by the DNA sequence of GCCTTGGACTACATCTCCTTGGATTACG-GTATGGACGTC [SEQ ID NO:29];

(v) a V$_H$ chain comprising a CDR1 region encoded by the DNA sequence of AGCTATGGCATGCAC [SEQ ID NO:7]; a CDR2 region encoded by the DNA sequence of CTTATATGGTATGATGGAAGTAATAAA-GAATATGCAGACTTC GTGAAGGGC [SEQ ID NO:18]; and a CDR3 region encoded by the DNA sequence of GATAGTCCCAAAATGAGGGCTG-GAAGTATGTTTCGCTACTACTACATGGACGTC [SEQ ID NO:30];

(vi) a V$_H$ chain comprising a CDR1 region encoded by the DNA sequence of AGTTACTGGATGCAC [SEQ ID NO:8]; a CDR2 region encoded by the DNA sequence of CGTATTAATAGTTATGGAATTAGCA-CAAGTTACGCGAACTCC GTGAAGGGC [SEQ ID NO:19]; and a CDR3 region encoded by the DNA sequence of GGAGAGCGCATAG-CAGCTCGTCTCTTGTCGGGCGGGTACGG-TATGGACGTC [SEQ ID NO:31];

(vii) a V$_H$ chain comprising a CDR1 region encoded by the DNA sequence of AGCTATGGCATGCAC [SEQ ID NO:9]; a CDR2 region encoded by the DNA sequence of GTGATATGGTATGATGGAAG-TAATAAGTACTATGCAGAGTCC GTGAAGGGC [SEQ ID NO:20]; and a CDR3 region encoded by the DNA sequence of GTCGTTAGCAGCAACCGG-TACTCTCTAAGCTACTATTATTACTA-CATGGACGTC [SEQ ID NO:32];

(viii) a V$_H$ chain comprising a CDR1 region encoded by the DNA sequence of AATTATGGCATGCAC [SEQ ID NO: 10]; a CDR2 region encoded by the DNA sequence of GTTATATGGTATGATGGAAG-TAATAAAAACTATGCAGACTCC GTGAAGGGC [SEQ ID NO:21]; and a CDR3 region encoded by the DNA sequence of GAACGTACTACGATGTCTG-GAGTGATCATTCCTCGCCGGTATTTTGACTAC; [SEQ ID NO:33]; and (ix) a V$_H$ chain comprising a CDR1 region encoded by the DNA sequence of AGCTATGGCATGCAC [SEQ ID NO:11]; a CDR2 region encoded by the DNA sequence of GTTATTTGGTATGATGGAAG-TAATAAATACTATGCAGACTCC GTGAAGGGC [SEQ ID NO:22]; and a CDR3 region encoded by the DNA sequence of GAAGTTACTATGGTTCGGG-GAGTTAGGCGTTACTACGGTATGGACGTC [SEQ ID NO:34], or a V$_H$ chain wherein at least one of said sequences has extended terminal regions.

2. The chimeric antibody V$_H$ chain according to claim 1, wherein said V$_H$ chain comprises a CDR1 region encoded by the DNA sequence of AGTGGTGGTCTCTACTGGGGC [SEQ ID NO: 1]; a CDR2 region encoded by the DNA sequence of AGTATATTTTATAGTGGGAGCACCTAC-TACAATCCCTC CCTCAAGAGC [SEQ ID NO:12]; and a CDR3 region encoded by the DNA sequence of CCAGGC-TATGGCGACACCTCGGTACGGAA-GAGGGTTTGGAATATGGACCTC [SEQ ID NO:23].

3. The chimeric antibody V$_H$ chain according to claim 1, wherein said V$_H$ chain comprises a CDR1 region encoded by the DNA sequence of AGTTCCTACTGGAGC [SEQ ID NO:2]; a CDR2 region encoded by the DNA sequence of TATATCTATTACAGTGGGAGCACCAAC-TACAACCCCTCCCTC AGGAGT [SEQ ID NO: 13]; and a CDR3 region encoded by the DNA sequence of GTTTTG-GTTTCCCGTACGATTTCACAGTACTC-CTATTACATGGACGTC [SEQ ID NO:25].

4. The chimeric antibody V$_H$ chain according to claim 1, wherein said V$_H$ chain comprises a CDR1 region encoded by the DNA sequence of GTTTACTACTGGACC [SEQ ID NO:4]; a CDR2 region encoded by the DNA sequence of GAAATCAATCATAGTGGAGGCGCCAAC-TACAATCCGTCC CTCAAGAGT [SEQ ID NO: 15]; and a CDR3 region encoded by the DNA sequence of GGCCG-GTCCCGTTATAGTGGTTACGGCTTC-TACTCCGGCATGGACGTC [SEQ ID NO:27].

5. The chimeric antibody V$_H$ chain according to claim 1, wherein said V$_H$ chain comprises a CDR1 region encoded by the DNA sequence of GGTTACTACTGGAGC [SEQ ID NO:6]; a CDR2 region encoded by the DNA sequence of GAAATCAGTCGTCGTGGAAGCACCAAC-TACAACCCGTCCCTCAAGAGT [SEQ ID NO: 17]; and a CDR3 region encoded by the DNA sequence of GCCTTG-GACTACATCTCCTTGGATTACGGTATGGACGTC [SEQ ID NO:29].

6. The chimeric antibody V$_H$ chain according to claim 1, wherein said V$_H$ chain comprises a CDR1 region encoded by the DNA sequence of AGCTATGGCATGCAC [SEQ ID NO:7]; a CDR2 region encoded by the DNA sequence of CTTATATGGTATGATGGAAGTAATAAA-GAATATGCAGACTTC GTGAAGGGC [SEQ ID NO: 18]; and a CDR3 region encoded by the DNA sequence of GATAGTCCCAAAATGAGGGCTGGAAG-TATGTTTCGCTACTACTACATGGACGTC [SEQ ID NO:30].

7. The chimeric antibody V$_H$ chain according to claim 1, wherein said V$_H$ chain comprises a CDR1 region encoded by the DNA sequence of AGTTACTGGATGCAC [SEQ ID NO:8]; a CDR2 region encoded by the DNA sequence of CGTATTAATAGTTATGGAATTAGCA-CAAGTTACGCGAACTCC GTGAAGGGC [SEQ ID NO: 19]; and a CDR3 region encoded by the DNA sequence of GGAGAGCGCATAGCAGCTCGTCTCT-TGTCGGGCGGGTACGGTATGGACGTC [SEQ ID NO:31].

8. The chimeric antibody V$_H$ chain according to claim 1, wherein said V$_H$ chain comprises a CDR1 region encoded by the DNA sequence of AGCTATGGCATGCAC [SEQ ID NO:9]; a CDR2 region encoded by the DNA sequence of GTGATATGGTATGATGGAAGTAATAAG-TACTATGCAGAGTCC GTGAAGGGC [SEQ ID NO:20]; and a CDR3 region encoded by the DNA sequence of GTCGTTAGCAGCAACCGG-TACTCTCTAAGCTACTATTATTACTACATGGACGTC [SEQ ID NO:32].

9. The chimeric antibody V$_H$ chain according to claim 1, wherein said V$_H$ chain comprises a CDR1 region encoded by the DNA sequence of AATTATGGCATGCAC [SEQ ID NO: 10]; a CDR2 region encoded by the DNA sequence of GTTATATGGTATGATGGAAG-TAATAAAAACTATGCAGACTCC GTGAAGGGC [SEQ ID NO:21]; and a CDR3 region encoded by the DNA sequence of GAACGTACTACGATGTCTGGAGTGAT-CATTCCTCGCCGGTATTTTGACTAC; [SEQ ID NO:33].

10. The chimeric antibody $V_H$ chain according to claim 1, wherein said $V_H$ chain comprises a CDR1 region encoded by the DNA sequence of AGCTATGGCATGCAC [SEQ ID NO:11]; a CDR2 region encoded by the DNA sequence of GTTATTTGGTATGATGGAAG-TAATAAATACTATGCAGACTCC GTGAAGGGC [SEQ ID NO:22]; and a CDR3 region encoded by the DNA sequence of GAAGTTACTATGGTTCGGGGAGTTAG-GCGTTACTACGGTATGGACGTC [SEQ ID NO:34].

11. A chimeric antibody $V_L$ chain against a Rhesus D antigen or an antigen binding fragment thereof comprising a CDR1, CDR2 and a CDR3 region, wherein said $V_L$ chain is selected from the group consisting of:
  (i) a $V_L$ chain comprising a CDR1 region encoded by the DNA sequence TCCGGAACCAGCTCCAACAT-TGGGAATAATTATGTATCC [SEQ ID NO:35]; a CDR2 region encoded by the DNA sequence GACAATAATAAGCGACCC TCA [SEQ ID NO:38]; and a CDR3 region encoded by the DNA sequence GCAACATGGGATAGCAGCCTGAGTGCT-GTGGTG [SEQ ID NO:41]; and
  (ii) a $V_L$ chain comprising a CDR1 region encoded by the DNA sequence GGGGGAAACAACATTGGACG-TAAAAGTGTGCAC [SEQ ID NO:37]; a CDR2 region encoded by the DNA sequence GGTGCTAGC-GACCGGCCCTCA [SEQ ID NO:40]; and a CDR3 region encoded by the DNA sequence CAGGTGTGG-GATAGTAGT AGTGCTCATCCGGGGGTGGTA [SEQ ID NO:42], or a $V_L$ chain wherein at least one of said sequences has extended terminal regions.

12. The chimeric antibody $V_L$ chain according to claim 11, wherein said $V_L$ chain comprises a CDR1 region encoded by the DNA sequence TCCGGAACCAGCTC-CAACATTGGGAATAATTATGTATCC [SEQ ID NO:35]; a CDR2 region encoded by the DNA sequence GACAATAATAAGCGACCC TCA [SEQ ID NO:38]; and a CDR3 region encoded by the DNA sequence GCAA-CATGGGATAGCAGCCTGAGTGCTGTGGTG [SEQ ID NO:41].

13. The chimeric antibody $V_L$ chain according to claim 11, wherein said $V_L$ chain comprises a CDR1 region encoded by the DNA sequence GGGGGAAACAACATTG-GACGTAAAAGTGTGCAC [SEQ ID NO:37]; a CDR2 region encoded by the DNA sequence GGTGCTAGCGAC-CGGCCCTCA [SEQ ID NO:40]; and a CDR3 region encoded by the DNA sequence CAGGTGTGGGATAG-TAGTAGTGCTCAT CCGGGGGTGGTA [SEQ ID NO:42].

14. A chimeric antibody molecule against the Rhesus (D) antigen or an antigen binding fragment thereof comprising a $V_H$ chain as defined in claim 1.

15. A chimeric antibody molecule against the Rhesus (D) antigen or an antigen binding fragment thereof comprising a $V_L$ chain as defined in claim 11.

16. A chimeric antibody molecule against the Rhesus (D) antigen or an antigen binding fragment thereof comprising a $V_H$ chain according to claim 1, and a chimeric antibody $V_L$ chain selected from the group consisting of:
  (i) a $V_L$ chain comprising a CDR1 region encoded by the DNA sequence TCCGGAACCAGCTCCAACAT-TGGGAATAATTATGTATCC [SEQ ID NO:35]; a CDR2 region encoded by the DNA sequence GACAATAATAAGCGACCC TCA [SEQ ID NO:38];

and a CDR3 region encoded by the DNA sequence GCAACATGGGATAGCAGCCTGAGTGCT-GTGGTG [SEQ ID NO:41]; and
  (ii) a $V_L$ chain comprising a CDR1 region encoded by the DNA sequence GGGGGAAACAACATTGGACG-TAAAAGTGTGCAC [SEQ ID NO:37]; a CDR2 region encoded by the DNA sequence GGTGCTAGC-GACCGGCCCTCA [SEQ ID NO:40]; and a CDR3 region encoded by the DNA sequence CAGGTGTGG-GATAGTAGT AGTGCTCATCCGGGGGTGGTA [SEQ ID NO:42], or a $V_L$ chain wherein at least one of said sequences has extended terminal regions.

17. A chimeric antibody molecule against the Rhesus (D) antigen or an antigen binding fragment thereof comprising a $V_L$ chain according to claim 11 and a $V_H$ chain selected from the group consisting of:
  (i) a $V_H$ chain comprising a CDR1 region encoded by the DNA sequence of AGTGGTGGTCTCTACTGGGGC [SEQ ID NO:1]; a CDR2 region encoded by the DNA sequence of AGTATATTTTATAGTGGGAGCAC-CTACTACAATCCCTC CCTCAAGAGC [SEQ ID NO:12]; and a CDR3 region encoded by the DNA sequence of CCAGGCTATGGCGACACCTCGG-TACGGAAGAGGGTTTGGAATATGGACCTC [SEQ ID NO:23];
  (ii) a $V_H$ chain comprising a CDR1 region encoded by the DNA sequence of AGTTCCTACTGGAGC [SEQ ID NO:2]; a CDR2 region encoded by the DNA sequence of TATATCTATTACAGTGGGAGCACCAAC-TACAACCCCTCCCTC AGGAGT [SEQ ID NO:13]; and a CDR3 region encoded by the DNA sequence of GTTTTGGTTTCCCGTACGATTTCACAG-TACTCCTATTACATGGACGTC [SEQ ID NO:25];
  (iii) a $V_H$ chain comprising a CDR1 region encoded by the DNA sequence of GTTTACTACTGGACC [SEQ ID NO:4]; a CDR2 region encoded by the DNA sequence of GAAATCAATCATAGTGGAGGCGCCAAC-TACAATCCGTCC CTCAAGAGT [SEQ ID NO:15]; and a CDR3 region encoded by the DNA sequence of GGCCGGTCCCGTTATAGTGGTTACGGCT-TCTACTCCGGCATGGACGTC [SEQ ID NO:27];
  (iv) a $V_H$ chain comprising a CDR1 region encoded by the DNA sequence of GGTTACTACTGGAGC [SEQ ID NO:6]; a CDR2 region encoded by the DNA sequence of GAAATCAGTCGTCGTGGAAGCACCAAC-TACAACCCGTCCCTC AAGAGT [SEQ ID NO:17]; and a CDR3 region encoded by the DNA sequence of GCCTTGGACTACATCTCCTTGGATTACG-GTATGGACGTC [SEQ ID NO:29];
  (v) a $V_H$ chain comprising a CDR1 region encoded by the DNA sequence of AGCTATGGCATGCAC [SEQ ID NO:7]; a CDR2 region encoded by the DNA sequence of CTTATATGGTATGATGGAAGTAATAAA-GAATATGCAGACTTC GTGAAGGGC [SEQ ID NO:18]; and a CDR3 region encoded by the DNA sequence of GATAGTCCCAAAATGAGGGCTG-GAAGTATGTTTCGCTACTACTACATGGACGTC [SEQ ID NO:30];
  (vi) a $V_H$ chain comprising a CDR1 region encoded by the DNA sequence of AGTTACTGGATGCAC [SEQ ID NO:8]; a CDR2 region encoded by the DNA sequence of CGTATTAATAGTTATGGAATTAGCA-CAAGTTACGCGAACTCC GTGAAGGGC [SEQ ID NO:19]; and a CDR3 region encoded by the DNA sequence of GGAGAGCGCATAG-

CAGCTCGTCTCTTGTCGGGCGGGTACGGTATGGACGTC [SEQ ID NO:31];

(vii) a $V_H$ chain comprising a CDR1 region encoded by the DNA sequence of AGCTATGGCATGCAC [SEQ ID NO:9]; a CDR2 region encoded by the DNA sequence of GTGATATGGTATGATGGAAGTAATAAGTACTATGCAGAGTCC GTGAAGGGC [SEQ ID NO:20]; and a CDR3 region encoded by the DNA sequence of GTCGTTAGCAGCAACCGGTACTCTCTAAGCTACTATTATTACTACATGGACGTC [SEQ ID NO:32];

(viii) a $V_H$ chain comprising a CDR1 region encoded by the DNA sequence of AATTATGGCATGCAC [SEQ ID NO:10]; a CDR2 region encoded by the DNA sequence of GTTATATGGTATGATGGAAGTAATAAAAACTATGCAGACTCC GTGAAGGGC [SEQ ID NO:21]; and a CDR3 region encoded by the DNA sequence of GAACGTACTACGATGTCTGGAGTGATCATTCCTCGCCGGTATTTTGACTAC; [SEQ ID NO:33]; and (ix) a $V_H$ chain comprising a CDR1 region encoded by the DNA sequence of AGCTATGGCATGCAC [SEQ ID NO:11]; a CDR2 region encoded by the DNA sequence of GTTATTTGGTATGATGGAAGTAATAAATACTATGCAGACTCC GTGAAGGGC [SEQ ID NO:22]; and a CDR3 region encoded by the DNA sequence of GAAGTTACTATGGTTCGGGGAGTTAGGCGTTACTACGGTATGGACGTC [SEQ ID NO:34], or a $V_H$ chain wherein at least one of said sequences has extended terminal regions.

18. An anti-Rhesus (D) reagent comprising a chimeric antibody as claimed in claim 14.

19. An anti-Rhesus (D) reagent comprising a chimeric antibody as claimed in claim 15.

20. An anti-Rhesus (D) reagent comprising a chimeric antibody as claimed in claim 16.

21. An anti-Rhesus (D) reagent comprising a chimeric antibody as claimed in claim 17.

22. A pharmaceutical composition comprising an antibody as claimed in claim 14 together with a pharmaceutically acceptable carrier or excipient.

23. A pharmaceutical composition comprising an antibody as claimed in claim 15 together with a pharmaceutically acceptable carrier or excipient.

24. A pharmaceutical composition comprising an antibody as claimed in claim 16 together with a pharmaceutically acceptable carrier or excipient.

25. A pharmaceutical composition comprising an antibody as claimed in claim 17 together with a pharmaceutically acceptable carrier or excipient.

26. A chimeric antibody molecule against the Rhesus (D) antigen or an antigen binding fragment thereof comprising a $V_H$ chain as defined in claim 1 and a $V_L$ chain of an antibody against the human RhD antigen.

27. A chimeric antibody molecule against the Rhesus (D) antigen or an antigen binding fragment thereof comprising a $V_L$ chain as defined in claim 11 and a $V_H$ chain of an antibody against the human RhD antigen.

28. An anti-Rhesus (D) reagent comprising a chimeric antibody as claimed in claim 26.

29. An anti-Rhesus (D) reagent comprising a chimeric antibody as claimed in claim 27.

30. A pharmaceutical composition comprising an antibody as claimed in claim 26 together with a pharmaceutically acceptable carrier or excipient.

31. A pharmaceutical composition comprising an antibody as claimed in claim 27 together with a pharmaceutically acceptable carrier or excipient.

* * * * *

UNITED STATES PATENT AND TRADEMARK OFFICE
CERTIFICATE OF CORRECTION

PATENT NO. : 5,919,910

DATED: : July 6, 1999

INVENTOR(S) : Nevin Campbell HUGHES-JONES

It is certified that error appears in the above-identified patent and that said Letters Patent is hereby corrected as shown below:

Substitute drawing Figure 1, as attached hereto, for drawing Figure 1.

Substitute drawing Figure 5, as attached hereto, for drawing Figure 5.

Substitute drawing Figure 6, as attached hereto, for drawing Figure 6.

Substitute drawing Figure 10, as attached hereto, for drawing Figure 10.

Substitute drawing Figure 11, as attached hereto, for drawing Figure 11.

Substitute drawing Figure 12, as attached hereto, for drawing Figure 12.

Signed and Sealed this

Twelfth Day of September, 2000

*Attest:*

Q. TODD DICKINSON

*Attesting Officer*       *Director of Patents and Trademarks*

```
  1  CAGGTGCAGCTGCAGGAGTCGGGCCCAGGACTGGTGAAGCCTTCGGAGACCCTGTCCGTC    60
     Q   V   Q   L   Q   E   S   G   P   G   L   V   K   P   S   E   T   L   S   V

61  ACCTGCACTGTCTCTGGTGGCTCCGTCAGTAGTTCCTACTGGAGCTGGATCCGGCAGCCC   120
     T   C   T   V   S   G   G   S   V   S   S   S   Y   W   S   W   I   R   Q   P
                                            <——————— CDR1 ———————>

121  CCAGGGAAGGGACCGGAGTGGATTGGGTATATCTATTACAGTGGGAGCACCAACTACAAC   180
     P   G   K   G   P   E   W   I   G   Y   I   Y   Y   S   G   S   T   N   Y   N
                                        <——————————————— CDR2

181  CCCTCCCTCAGGAGTCGAGTCACCATATCAGTAGACACGTCCAAGAACCAGTTCTCCCTG   240
     P   S   L   R   S   R   V   T   I   S   V   D   T   S   K   N   Q   F   S   L
     ———————>

241  AAGCTGGGCTCTGTGACCGCTGCGGACACGGCCGTGTATTACTGTGCGAGAGTTTTGGTT   300
     K   L   G   S   V   T   A   A   D   T   A   V   Y   Y   C   A   R   V   L   V
                                                                <—————————

301  TCCCGTACGATTTCACAGTACTCCTATTACATGGACGTCTGGGGCAAAGGGACCACGGTC   360
     S   R   T   I   S   Q   Y   S   Y   Y   M   D   V   W   G   K   G   T   T   V
     ——————————— CDR3 ——————————————>

361  ACCGTGTCCTCA   372
     T   V   S   S
```

FIG. 5

```
  1  ———PCR PRIMER———        CGCAGGACTGTGAAGCCTTCGGAGACCCTGTCCCTC  60
                              A  G  L  L  K  P  S  E  T  L  S  L

61  ACCTGCGCTGTCTATGGTGGGTCCTTCAGTGGTTACTACTGGAGCTGGATCCGCCAGCCT 120
      T  C  A  V  Y  G  G  S  F  S  G  Y  Y  W  S  W  I  R  Q  P
                                 <———  CDR1  ———>

121  CCAGGGAAGGGGCTGGAGTGGATTGGGGAAATCAATCATAGTGGAAGGACCAACTACAAC 180
      P  G  K  G  L  E  W  I  G  E  I  N  H  S  G  R  T  N  Y  N
                                    <——————— CDR2

181  CCGTCCCTCAAGACTCGAGTCACCATATCAGTAGACACGTCCAAGAACCAGTTCTCCCTG 240
      P  S  L  K  T  R  V  T  I  S  V  D  T  S  K  N  Q  F  S  L
     ———————>

241  AAGCTGAGTTCTGTGACCGCCGCGGACACGGCTGTGTATTACTGTGCGAGACTGTGGCTC 300
      K  L  S  S  V  T  A  A  D  T  A  V  Y  Y  C  A  R  L  W  L

301  GATGGACACATGGGGTACAAGTTTGACTACTGGGGCCAGGGAACCCT  ———PCR PRIMER——— 360
      D  G  H  G  Y  K  F  D  Y  W  G  Q  G  T  L
     ———————  CDR3 ———>
```

FIG. 6

```
1    ———PCR PRIMER———GGGAGGCGTGGTCCAGCCTGGGAGGTTCCTGAGACTC  60
                     G G V V Q P G R F L R L

61   TCCTGTGCAGCGTCTGGATTCACCTTCAGTAGCTATGGCATGCACTGGGTCCGCCAGGCT 120
     S C A A S G F T F S S Y G M H W V R Q A
                         ←———CDR1———→

121  CCAGGCAAGGGGCTGGAGTGGGTGGCACTTATATGGTATGATGGAAGTAATAAAGAATAT 180
     P G K G L E W V A L I W Y D G S N K E Y
                         ←————————CDR2————————

181  GCAGACTTCGTGAAGGGCCGATTCACCATCTCCAGAGACAATTCCAAGAATACACTGTAT 240
     A D F V K G R F T I S R D N S K N T L Y
     ————————→

241  CTGCAAATGAACAGCCTGAGAGCCGAGGACACGGCTGTGTATTACTGTGCGACAGATAGT 300
     L Q M N S L R A E D T A V Y Y C A T D S
                                         ←

301  CCCAAAATGAGGGCTGGAAGTATGTTTCGCTACTACTACATGGACGTCTGGGGCAAAGGG 360
     P K M R A G S M F R Y Y Y Y M D V W G K G
     ————CDR3————————————————————→

361  ACCAC———PCR PRIMER———  381
     T
```

FIG. 10

```
1    ――――PCR PRIMER――――― GGGAGGCTTAGTTCAGCCTGGGGGGTCCCTGAGACTC   60
                               G  G  L  V  Q  P  G  G  G  S  L  R  L

61   TCCTGTGCAGCCTCTGGATTCACCTTCAGTAGTTACTGGATGCACTGGGTCCGCCAAGCT  120
      S  C  A  A  S  G  F  T  F  S  S  Y  W  M  H  W  V  R  Q  A
                                         <―――― CDR1 ――――>

121  CCAGGGAAGGGGCTGGTGTGGGTCTCACGTATTAATAGTTATGGAATTAGCACAAGTTAC  180
      P  G  K  G  L  V  W  V  S  R  I  N  S  Y  G  I  S  T  S  Y
                                   <――――――――――― CDR2

181  GCGAACTCCGTGAAGGGCCGATTCACCATCTCCAGAGACAACGCCAAGAACACGCTGTAT  240
      A  N  S  V  K  G  R  F  T  I  S  R  D  N  A  K  N  T  L  Y
     ―――――>

241  CTGCAAATGAACACTCTGAGAGCCGAGGACACGGCTGTGTATTACTGTGCAAGAGGAGAG  300
      L  Q  M  N  T  L  R  A  E  D  T  A  V  Y  Y  C  A  R  G  E
                                                             <―

301  CGCATAGCAGCTCGTCTCTTGTCGGGGGTACGGTATGGACGTCTGGGGCCAAGGGACC    360
      R  I  A  A  R  L  L  S  G  G  Y  G  M  D  V  W  G  Q  G  T
     ――――――――――――――― CDR3 ―――――――――――――――>

361  AC                                                            378
     ―――PCR PRIMER―――>
```

FIG. 11

```
                          ─────PCR PRIMER─────      GGGAGGCGTGGTCCAGCCTGGGAGGTCCCTGAGACTC  60
  1                                                  G  V  V  Q  P  G  R  S  L  R  L

61   TCCTGTGCAGCGTCTGGATTCACCTTTAGTAGCTATGGCATGCACTGGGTCCGCCAGGCT                      120
       S  C  A  A  S  G  F  T  F  S  S  Y  G  M  H  W  V  R  Q  A
                                 ←──────CDR1──────→

121   CCAGGCAAGGGGCTGGAGTGGGTGGCAGTGATATGGTATGATGGAAGTAATAAGTACTAT                      180
       P  G  K  G  L  E  W  V  A  V  I  W  Y  D  G  S  N  K  Y  Y
                                        ←──────────CDR2

181   GCAGAGTCCGTGAAGGGCCGATTCACCATCTCCAGAGACAATTCCAAGAACACGCTGTAT                      240
       A  E  S  V  K  G  R  F  T  I  S  R  D  N  S  K  N  T  L  Y
              ──→

241   CTGCAAATGAACAGCCTGAGAGCCGAGGACACGGCTGTGTATTACTGTGCGAGAGTCGTT                      300
       L  Q  M  N  S  L  R  A  E  D  T  A  V  Y  Y  C  A  R  V  V
                                                                ←──

301   AGCAGCAACCGGTACTCTCTAAGCTACTATTATTACTACATGGACGTCTGGGGCAAAGGG                      360
       S  S  N  R  Y  S  L  S  Y  Y  Y  Y  Y  Y  M  D  V  W  G  K  G
      ──────────────────CDR3──────────────────→

361   ACCAC      ─────PCR PRIMER─────  381
       T
```

FIG. 12

SEQUENCE LISTING (1) GENERAL INFORMATION:

(iii) NUMBER OF SEQUENCES: 55

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

AGTGGTGGTC TCTACTGGGG C                            21

(2) INFORMATION FOR SEQ ID NO:2:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

AGTTCCTACT GGAGC                                15

(2) INFORMATION FOR SEQ ID NO:3:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

GGTTACTACT GGAGC                                15

(2) INFORMATION FOR SEQ ID NO:4:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

GTTTACTACT GGACC                                15

(2) INFORMATION FOR SEQ ID NO:5:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

GGTTACTACT GGAAC                                                              15

(2) INFORMATION FOR SEQ ID NO:6:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

GGTTACTACT GGAGC                                                              15

(2) INFORMATION FOR SEQ ID NO:7:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

AGCTATGGCA TGCAC                                                              15

(2) INFORMATION FOR SEQ ID NO:8:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

AGTTACTGGA TGCAC                                                              15

(2) INFORMATION FOR SEQ ID NO:9:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:9:

AGCTATGGCA TGCAC                                                              15

(2) INFORMATION FOR SEQ ID NO:10:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

AATTATGGCA TGCAC                                                          15

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGCTATGGCA TGCAC                                                          15

(2) INFORMATION FOR SEQ ID NO:12:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AGTATATTTT ATAGTGGGAG CACCTACTAC AATCCCTCCC TCAAGAGC                       48

(2) INFORMATION FOR SEQ ID NO:13:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TATATCTATT ACAGTGGGAG CACCAACTAC AACCCCTCCC TCAGGAGT                       48

(2) INFORMATION FOR SEQ ID NO:14:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GAAATCAATC ATAGTGGAAG GACCAACTAC AACCCGTCCC TCAAGACT                       48

(2) INFORMATION FOR SEQ ID NO:15:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
GAAATCAATC ATAGTGGAGG CGCCAACTAC AATCCGTCCC TCAAGAGT                48
```

(2) INFORMATION FOR SEQ ID NO:16:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
GAAATCATTC ATAGTGGAAG CACCAACTAC AACCCGTCCC TCAAGAGT                48
```

(2) INFORMATION FOR SEQ ID NO:17:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
GAAATCAGTC GTCGTGGAAG CACCAACTAC AACCCGTCCC TCAAGAGT                48
```

(2) INFORMATION FOR SEQ ID NO:18:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
CTTATATGGT ATGATGGAAG TAATAAAGAA TATGCAGACT TCGTGAAGGG C            51
```

(2) INFORMATION FOR SEQ ID NO:19:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
CGTATTAATA GTTATGGAAT TAGCACAAGT TACGCGAACT CCGTGAAGGG C            51
```

(2) INFORMATION FOR SEQ ID NO:20:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
GTGATATGGT ATGATGGAAG TAATAAGTAC TATGCAGAGT CCGTGAAGGG C            51
```

(2) INFORMATION FOR SEQ ID NO:21:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GTTATATGGT ATGATGGAAG TAATAAAAAC TATGCAGACT CCGTGAAGGG C          51

(2) INFORMATION FOR SEQ ID NO:22:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GTTATTTGGT ATGATGGAAG TAATAAATAC TATGCAGACT CCGTGAAGGG C          51

(2) INFORMATION FOR SEQ ID NO:23:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CCAGGCTATG GCGACACCTC GGTACGGAAG AGGGTTTGGA ATATGGACCT C          51

(2) INFORMATION FOR SEQ ID NO:24:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GTTTTGGTTT CCCGTACCAT TTCACAGTAC TCCTATTACA TGGACGTC             48

(2) INFORMATION FOR SEQ ID NO:25:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GTTTTGGTTT CCCGTACGAT TTCACAGTAC TCCTATTACA TGGACGTC             48

(2) INFORMATION FOR SEQ ID NO:26:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CTGTGGCTCG ATGGACATGG GTACAAGTTT GACTAC                                36

(2) INFORMATION FOR SEQ ID NO:27:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:27:

GGCCGGTCCC GTTATAGTGG TTACGGCTTC TACTCCGGCA TGGACGTC                   48

(2) INFORMATION FOR SEQ ID NO:28:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:28:

GGCTTAGAAC GTCCGATTAG GAACCAGCTG CTAAACCGTC TCGGTTACTA CATGGACGTC      60

(2) INFORMATION FOR SEQ ID NO:29:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:29:

GCCTTGGACT ACATCTCCTT GGATTACGGT ATGGACGTC                             39

(2) INFORMATION FOR SEQ ID NO:30:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:30:

GATAGTCCCA AAATGAGGGC TGGAAGTATG TTTCGCTACT ACTACATGGA CGTC            54

(2) INFORMATION FOR SEQ ID NO:31:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:31:

```
GGAGAGCGCA TAGCAGCTCG TCTCTTGTCG GGCGGGTACG GTATGGACGT C            51

(2) INFORMATION FOR SEQ ID NO:32:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:32:

GTCGTTAGCA GCAACCGGTA CTCTCTAAGC TACTATTATT ACTACATGGA CGTC          54

(2) INFORMATION FOR SEQ ID NO:33:

(i) SEQUENCE CHARACTERISTICS:
         (A) LENGTH: 51 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:33:

GAACGTACTA CGATGTCTGG AGTGATCATT CCTCGCCGGT ATTTTGACTA C             51

(2) INFORMATION FOR SEQ ID NO:34:

(i) SEQUENCE CHARACTERISTICS:
         (A) LENGTH: 48 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:34:

GAAGTTACTA TGGTTCGGGG AGTTAGGCGT TACTACGGTA TGGACGTC                 48

(2) INFORMATION FOR SEQ ID NO:35:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:35:

TCCGGAACCA GCTCCAACAT TGGGAATAAT TATGTATCC                           39

(2) INFORMATION FOR SEQ ID NO:36:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:36:

GGGGGAAACA ACATTGGGCG TAAAAGTGTG CAC                                 33

(2) INFORMATION FOR SEQ ID NO:37:
```

(i) SEQUENCE CHARACTERISTICS:
             (A) LENGTH: 33 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:37:

GGGGGAAACA ACATTGGACG TAAAAGTGTG CAC                                             33

(2) INFORMATION FOR SEQ ID NO:38:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:38:

GACAATAATA AGCGACCCTC A                                                         21

(2) INFORMATION FOR SEQ ID NO:39:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:39:

GGTGCTAGCG AGCGGCCCTC A                                                         21

(2) INFORMATION FOR SEQ ID NO:40:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:40:

GGTGCTAGCG ACCGGCCCTC A                                                         21

(2) INFORMATION FOR SEQ ID NO:41:

(i) SEQUENCE CHARACTERISTICS:
             (A) LENGTH: 33 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:41:

GCAACATGGG ATAGCAGCCT GAGTGCTGTG GTG                                             33

(2) INFORMATION FOR SEQ ID NO:42:

(i) SEQUENCE CHARACTERISTICS:
             (A) LENGTH: 39 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:42:

CAGGTGTGGG ATAGTAGTAG TGCTCATCCG GGGGTGGTA                                  39

(2) INFORMATION FOR SEQ ID NO:43:

(i) SEQUENCE CHARACTERISTICS:
            (A) LENGTH: 333 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:43:

CAGTCTGTGT TGACGCAGCC GCCCTGAGTG TCTGCGGCCC CAGGACAGAA GGTCACCATC          60

TCCTGCTCCG GAACCAGCTC CAACATTGGG AATAATTATG TATCCTGGTA TCAGCAGCTC         120

CCAGGAACAG CCCCCAAACT CCTCATTTAT GACAATAATA AGCGACCCTC AGGGATTCCT         180

GACCGATTCT CTGGCTCCAA GTCTGGCACG TCAGCCACCC TGGGCATCAC CGGACTCCGG         240

ACTGGGGACG AGGCCGATTA TTACTGCGCA ACATGGGATA GCAGCCTGAG TGCTGTGGTG         300

TTCGGCGGAG GGACCAAGCT GACCGTCCTA AGT                                     333

(2) INFORMATION FOR SEQ ID NO:44:

(i) SEQUENCE CHARACTERISTICS:
            (A) LENGTH: 333 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:44:

TCCTATGTGC TGACTCAGCC ACCCTCGGTG TCAGTGGCCC CAGGACAGAC GGCCAGGATT          60

ACCTGTGGGG GAAACAACAT TGGACGTAAA AGTGTGCACT GGTACCAGCA GAAGCCAGGC         120

CAGGCCCCTG TGCTGGTCGT CTATGGTGCT AGCGACCGGC CCTCAGGGAT CCCTGAGCGA         180

TTCTCTGGCT CCAACTCTGG GAACACGGCC ACCCTGACCA TCAGCAGGGT CGCAGCCGGG         240

GATGAGGCCG ACTATTACTG TCAGGTGTGG GATAGTAGTA GTGCTCATCC GGGGGTGGTA         300

TTCGGCGGAG GGACCAAGCT GACCGTCCTA GGT                                     333

(2) INFORMATION FOR SEQ ID NO:45:

(i) SEQUENCE CHARACTERISTICS:
            (A) LENGTH: 381 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:45:

CAGCTGCGGC TGCAGGAGTC GGGCCCAGGA CTGGTGAAGC CTTCGGAGAC CCTGTCCCTC          60

ACCTGCAGTG TCTCTGGTGG CTCCGTCAGC AGTGGTGGTC TCTACTGGGG CTGGGTCCGC         120

CAGCCCCCAG GAAGGGGCT CGAATGGATT GGCAGTATAT TTTATAGTGG GAGCACCTAC          180

TACAATCCCT CCCTCAAGAG CCGAGTCACC ATATCCGTAG ACACGTTGAA GAATAACTTC         240

TCCCTGAAGC TGAGTTCTGT GACCGCCGCA GACACGGCTG TTTATTACTG TACGAGACCA         300

GGCTATGGCG ACACCTCGGT ACGGAAGAGG GTTTGGAATA TGGACCTCTG GGGCCAAGGG      360

ACCACGGTCA CCGTCTCCTC G                                                381

(2) INFORMATION FOR SEQ ID NO:46:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

CAGGTGCAGC TGCAGGAGTC GGGCCCAGGA CTGGTGAAGC CTTCGGAGAC CCTGTCCGTC       60

ACCTGCACTG TCTCTGGTGG CTCCGTCAGT AGTTCCTACT GGAGCTGGAT CCGGCAGCCC      120

CCAGGGAAGG GACCGGAGTG GATTGGGTAT ATCTATTACA GTGGGAGCAC CAACTACAAC      180

CCCTCCCTCA GGAGTCGAGT CACCATATCA GTAGACACGT CCAAGAACCA GTTCTCCCTG      240

AAGCTGGGCT CTGTGACCGC TGCGGACACG GCCGTGTATT ACTGTGCGAG AGTTTTGGTT      300

TCCCGTACGA TTTCACAGTA CTCCTATTAC ATGGACGTCT GGGGCAAAGG GACCACGGTC      360

ACCGTGTCCT CA                                                         372

(2) INFORMATION FOR SEQ ID NO:47:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..321
        (D) OTHER INFORMATION: /note= "Nucleotides 1-321 corres.
            to nucleotides 24-344 of Fig. 6/14. Nucleotides
            1-23 and 345-360 represent PCR primers."

(xi) SEQUENCE DESCRIPTION: SEQ ID NO:47:

CGCAGGACTG TTGAAGCCTT CGGAGACCCT GTCCCTCACC TGCGCTGTCT ATGGTGGGTC       60

CTTCAGTGGT TACTACTGGA GCTGGATCCG CCAGCCTCCA GGGAAGGGGC TGGAGTGGAT      120

TGGGAAATC AATCATAGTG GAAGGACCAA CTACAACCCG TCCCTCAAGA CTCGAGTCAC       180

CATATCAGTA GACACGTCCA AGAACCAGTT CTCCCTGAAG CTGAGTTCTG TGACCGCCGC      240

GGACACGGCT GTGTATTACT GTGCGAGACT GTGGCTCGAT GGACATGGGT ACAAGTTTGA      300

CTACTGGGGC CAGGGAACCC T                                               321

(2) INFORMATION FOR SEQ ID NO:48:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

CAGGTGCATC TACAGCAGTG GGGCACAGGG CTGTTGAAGC CTTCGGAGAC CCTGTCCCTC       60

ACCTGCGCTG TCCATGGTGG GTCCTTCAAT GTTTACTACT GGACCTGGAT CCGCCAGCCC      120

```
CCAGGAAAGG CGCTGGAGTG GATTGGGGAA ATCAATCATA GTGGAGGCGC CAACTACAAT      180

CCGTCCCTCA AGAGTCGAGT CACCATGTCA GCAGACACGT CCAAGAACCA GTTCTCCCTG      240

AAACTGACCT CTGTGACCGC CGCGGACACG GCTGTGTTTT ATTGTGCGAG AGGCCGGTCC      300

CGTTATAGTG GTTACGGCTT CTACTCCGGC ATGGACGTCT GGGGCCCAGG GACCACGGTC      360

ACCGTCTCCT CA                                                         372
```

(2) INFORMATION FOR SEQ ID NO:49:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

```
CAGGTGCAGC TACAGCAGTG GGGCGCAGGA CTGTTGAAGC CTTCGGAGAC CCTGTCCCTC       60

ACCTGCGCTG TCTATGGTGG GTCCTTCAGT GGTTACTACT GGAACTGGAT CCGCCAGCCC      120

CCAGGGAAGG GGCTGGAGTG GATTGGGGAA ATCATTCATA GTGGAAGCAC CAACTACAAC      180

CCGTCCCTCA AGAGTCGAGT CACCATGTCA GTAGACACGT CCAAGAACCA GTTCTCCCTG      240

AAGCTGAGCT CTGTGACCGC CGCGGACACG GCTGTGTATT ACTGTGCGAG AGGCTTAGAA      300

CGTCCGATTA GGAACCAGCT GCTAAACCGT CTCGGTTACT ACATGGACGT CTGGGGCAAA      360

GGGACCACGG TCACCGTCTC CTCA                                            384
```

(2) INFORMATION FOR SEQ ID NO:50:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

```
CAGGTGCAGC TACAGCAGTG GGGCGCAGGA CTGTTGAAGC CTTCGGAGAC CCTGTCCCTC       60

ACCTGCGCTG TCTATGGTGG GTCCTTCAGT GGTTACTACT GGAGCTGGAT CCGCCAGCCC      120

CCAGGGAAGG GGCTGGAGTG GATTGGGGAA ATCAGTCGTC GTGGAAGCAC CAACTACAAC      180

CCGTCCCTCA AGAGTCGAGT CGCCATATCA GTAGACACGT CCAAGAACCA GTTCTCCCTG      240

AAGGTGAGGT CTGTGACCGC CGCGGACACG GCTGTGTATT ACTGTGCGAG AGCCTTGGAC      300

TACATCTCCT TGGATTACGG TATGGACGTC TGGGGCCAAG GGACCACGGT CACCGTCTCC      360

TCA                                                                   363
```

(2) INFORMATION FOR SEQ ID NO:51:

(i) SEQUENCE CHARACTERISTICS:
        (A) LENGTH: 342 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..342
        (D) OTHER INFORMATION: /note= "Nucleotides 1-381 corres.
            to nucleotides 24-365 of Fig. 10/14. Nucleotides 1-23 and 366-381 represent PCR primers."

(xi) SEQUENCE DESCRIPTION: SEQ ID NO:51:

```
GGGAGGCGTG GTCCAGCCTG GGAGGTTCCT GAGACTCTCC TGTGCAGCGT CTGGATTCAC      60

CTTCAGTAGC TATGGCATGC ACTGGGTCCG CCAGGCTCCA GGCAAGGGGC TGGAGTGGGT     120

GGCACTTATA TGGTATGATG GAAGTAATAA AGAATATGCA GACTTCGTGA AGGGCCGATT     180

CACCATCTCC AGAGACAATT CCAAGAATAC ACTGTATCTG CAAATGAACA GCCTGAGAGC     240

CGAGGACACG GCTGTGTATT ACTGTGCGAC AGATAGTCCC AAAATGAGGG CTGGAAGTAT     300

GTTTCGCTAC TACTACATGG ACGTCTGGGG CAAAGGGACC AC                        342
```

(2) INFORMATION FOR SEQ ID NO:52:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..339
        (D) OTHER INFORMATION: /note= "Nucleotides 1-378 corres.
            to nucleotides 24-362 of Fig. 11/14. Nucleotides
            1-23 and 363-378 represent PCR primers."

(xi) SEQUENCE DESCRIPTION: SEQ ID NO:52:

```
GGGAGGCTTA GTTCAGCCTG GGGGGTCCCT GAGACTCTCC TGTGCAGCCT CTGGATTCAC      60

CTTCAGTAGT TACTGGATGC ACTGGGTCCG CCAAGCTCCA GGGAAGGGGC TGGTGTGGGT     120

CTCACGTATT AATAGTTATG GAATTAGCAC AAGTTACGCG AACTCCGTGA AGGGCCGATT     180

CACCATCTCC AGAGACAACG CCAAGAACAC GCTGTATCTG CAAATGAACA CTCTGAGAGC     240

CGAGGACACG GCTGTGTATT ACTGTGCAAG AGGAGAGCGC ATAGCAGCTC GTCTCTTGTC     300

GGGCGGGTAC GGTATGGACG TCTGGGGCCA AGGGACCAC                            339
```

(2) INFORMATION FOR SEQ ID NO:53:

(i) SEQUENCE CHARACTERISTICS:
        (A) LENGTH: 342 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..342
        (D) OTHER INFORMATION: /note= "Nucleotides 1-381 corres.
            to nucleotides 24-365 of Fig. 12/14. Nucleotides
            1-23 and 366-381 represent PCR primers."

(xi) SEQUENCE DESCRIPTION: SEQ ID NO:53:

```
GGGAGGCGTG GTCCAGCCTG GGAGGTCCCT GAGACTCTCC TGTGCAGCGT CTGGATTCAC      60

CTTTAGTAGC TATGGCATGC ACTGGGTCCG CCAGGCTCCA GGCAAGGGGC TGGAGTGGGT     120

GGCAGTGATA TGGTATGATG GAAGTAATAA GTACTATGCA GAGTCCGTGA AGGGCCGATT     180

CACCATCTCC AGAGACAATT CCAAGAACAC GCTGTATCTG CAAATGAACA GCCTGAGAGC     240

CGAGGACACG GCTGTGTATT ACTGTGCGAG AGTCGTTAGC AGCAACCGGT ACTCTCTAAG     300

CTACTATTAT TACTACATGG ACGTCTGGGG CAAAGGGACC AC                        342
```

(2) INFORMATION FOR SEQ ID NO:54:

(i) SEQUENCE CHARACTERISTICS:
    (A) LENGTH: 339 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..339
    (D) OTHER INFORMATION: /note= "Nucleotides 1-378 corres.
        to nucleotides 24-362 of Fig. 13/14. Nucleotides
        1-23 and 363-378 represent PCR primers."

(xi) SEQUENCE DESCRIPTION: SEQ ID NO:54:

```
GGGAGGCGTG GTCCAGCCTG GGAGGTCCCT GAGACTCTCC TGTGCAGCGT CTGGATTCAC      60

CTTCAATAAT TATGGCATGC ACTGGGTCCG CCAGGCTCCA GGCAAGGGGC TGGAGTGGGT     120

GGCAGTTATA TGGTATGATG GAAGTAATAA AAACTATGCA GACTCCGTGA AGGGCCGATT     180

CACCATCTCC AGAGACAATT CCAAGAACAC GCTGTATCTG CAAATGAACA GCCTGAGAGC     240

CGAGGACACG GCTGTGTATT ACTGTGCGAG AGAACGTACT ACGATGTCTG GAGTGATCAT     300

TCCTCGCCGG TATTTTGACT ACTGGGGCCA GGGAACCCG                            339
```

(2) INFORMATION FOR SEQ ID NO:55:

(i) SEQUENCE CHARACTERISTICS:
    (A) LENGTH: 335 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..335
    (D) OTHER INFORMATION: /note= "Nucleotides 1-375 corres.
        to nucleotides 24-359 of Fig. 14/14. Nucleotides
        1-23 and 360-375 represent PCR primers."

(xi) SEQUENCE DESCRIPTION: SEQ ID NO:55:

```
GGGGGCGTGG TCCAGCCTGG GAGGTCCCTG AGACTCTCCT GTGCAGCGTC TGGATTCACC      60

TTCAGTAGCT ATGGCATGCA CTGGGTCCGC CAGGCTCCAG GCAAGGGGCT GGAGTGGGTG     120

GCAGTTATTT GGTATGATGG AAGTAATAAA TACTATGCAG ACTCCGTGAA GGGCCGATTC     180

ACCATCTCCA GAGACAATTC CAAGAACACG CTGTATCTGC AAATGAACAG CCTGAGAGCC     240

GAGGACACGG CTGTGTATTA CTGTGCGAGA GAAGTTACTA TGGTTCGGGG AGTTAGGCGT     300

TACTACGGTA TGGACGTCTG GGGCCCAGGG ACCAC                                335
```